United States Patent [19]
Hama et al.

[11] Patent Number: 5,919,654
[45] Date of Patent: *Jul. 6, 1999

[54] SECRETION SIGNAL GENE AND EXPRESSION VECTOR CONTAINING IT

[75] Inventors: Yuko Hama; Hideki Tohda; Hiroko Tsukamoto; Kiyokazu Nikaido; Hiromichi Kumagai, all of Yokohama, Japan

[73] Assignee: Asahi Glass Company Ltd., Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/716,317

[22] PCT Filed: Feb. 1, 1996

[86] PCT No.: PCT/JP96/00198

§ 371 Date: Oct. 2, 1996

§ 102(e) Date: Oct. 2, 1996

[87] PCT Pub. No.: WO96/23890

PCT Pub. Date: Aug. 8, 1996

[30] Foreign Application Priority Data

Feb. 3, 1995 [JP] Japan ........................ 7-17167

[51] Int. Cl.⁶ .................................................. C12N 15/00
[52] U.S. Cl. ................ 435/69.1; 435/252.3; 435/254.11; 435/320.1; 536/23.1; 536/24.1
[58] Field of Search ................... 536/23.1, 24.1; 435/69.1, 252.3, 254.11, 320.1

[56] References Cited

U.S. PATENT DOCUMENTS

| | | | |
|---|---|---|---|
| 5,024,941 | 6/1991 | Maine et al. | 435/69.9 |
| 5,712,113 | 1/1998 | Chung et al. | 435/69.1 |

FOREIGN PATENT DOCUMENTS

WO 90/01063  2/1990  WIPO.

OTHER PUBLICATIONS von Heijne (1986) Nucleic Acids Res., vol. 14, No. 11, pp. 4683–4690, 1986.

Imai et al. (1994) Genes and Development, vol. 8, pp. 328–338, 1994.

Tohda et al. (1994) Gene, vol. 150, pp. 275–280, 1994.

*Primary Examiner*—Robert A. Wax
*Assistant Examiner*—Enrique D. Longton
*Attorney, Agent, or Firm*—Oblon, Spivak, McClelland, Maier & Neustadt, P.C.

[57] ABSTRACT

A secretion signal gene having a base sequence encoding a polypeptide functional as a secretion signal in fission yeast *Schizosaccharomyces pombe* (hereinafter referred to as *S. pombe*), an expression vector having the gene and a foreign protein structural gene, a multicloning vector for construction of the expression vector which has the secretion signal gene, and efficient secretory production of the foreign protein structural gene product by *S. pombe* and the like.

10 Claims, 5 Drawing Sheets

SECRETION SIGNAL GENE AND EXPRESSION VECTOR CONTAINING IT

This application claims priority to PCT/JP96/00198 filed Feb. 1, 1996 and Japanese Patent No. 7/17167 filed Feb. 3, 1995.

TECHNICAL FIELD

The present invention relates to a secretion signal gene having a base sequence encoding a polypeptide derived from the secretion signal of a precursor of a mating pheromone (P-factor), which concerns mating of fission yeast *Schizosaccharomyces pombe* (hereinafter referred to as *S. pombe*). The present invention also relates to an expression vector containing the secretion signal gene and a foreign protein structural gene, and efficient secretory production of the foreign protein structural gene product by *S. pombe* or the like.

BACKGROUND ART

Hitherto, production of foreign proteins utilizing genetic recombination technology has been extensively conducted by using microorganisms such as *Escherichia coli*, *Saccharomyces cerevisiae* or Bacillus, animal cells, plant cells and insect cells. As such foreign proteins, various biogenic proteins are considered to be accessible, and many of them have been industrially produced by using these living organisms for medical use so far.

However, methods employing procaryotes are not effective for all polypeptides, and it is not always easy to reproduce the complicated post-translational modification of eucaryotic proteins and to reproduce the natural steric structures. In addition, *Escherichia coli* has a characteristic endotoxin, which might contaminate end products. On the other hand, as for methods employing animal, plant or insect cells, these cells are more difficult to handle than microorganisms, their culture is costly, and production efficiency is low. For this reason, yeasts, eucaryotic microorganisms, are considered as the best for production of foreign proteins, especially eucaryotic proteins. Their culture methods are well established, and they do not contain endotoxins. Therefore, expression vectors for use in various yeast hosts have been developed so far (Romanos, M. A. et al., Yeast 8, 423–488, 1992).

Among various yeasts, *S. pombe* is considered to be closer to higher animals in various properties such as cell cycle, chromosomal structure and RNA splicing than other yeasts inclusive of *Saccharomyces cerevisiae*. The post-translational modification such as acetylation, phosphorylation and glycosylation of proteins produced in *S. pombe* seems fairly similar to that in animal cells (Russell, P. R. and Nurse, P., Cell 45, 781–782, 1986; Kaufer, N. F. et al, Nature 318, 78–80, 1985; Chappell, T. G. and Warren, G., J. Cell. Biol. 109, 2693–2702, 1989). Therefore, use of *S. pombe* as a host for expression of a foreign protein is expected to provide a gene product closer to its natural form, like that produced by animal cells. Since yeasts have a lot of commonness in their culture methods, knowledges about other yeasts can be easily applied to the yeast. Therefore, it is obviously advantageous to use *S. pombe* for production of a foreign protein by using microbiological methods and the DNA recombination technique.

However, *S. pombe* is far behind *Escherichia coli* and *Saccharomyces cerevisiae* in studies on genetic recombination using them. Especially, with respect to gene expression in *S. pombe*, only a small number of studies have been reported (Japanese Unexamined Patent Publications Nos. 181397/1986, 283288/1990 and 63596/1992). This is because development of expression vectors which have powerful promoters, are stable in *S. pombe* cells and are suitable and convenient for introduction of a gene has been retarded. Recent development of vectors for the fission yeast with a high expressivity which contains an animal virus-derived promoter region eventually opened the way to mass production of foreign proteins by *S. pombe* (Japanese Unexamined Patent Publications Nos. 15380/1993 and 163373/1995, which disclose inventions of the present inventors). This technique enabled many intracellular proteins to be produced easily and therefore is fairly useful.

Production of (foreign) eucaryotic secretory proteins by yeasts scarcely succeeded so far because yeasts can hardly recognize inherent signal sequences of foreign secretory proteins and therefore can not secrete the products from the cells into culture media. Further, at the time of purification, it was necessary that after cell rupture, the desired protein should be isolated from various coexistent cell components to avoid inactivation. Secretory production of a foreign protein is not only preferable in view of the easiness of purification, but also advantageous in that the product is identical or fairly similar to its naturally occurring counterpart in steric structure, because the protein to be secreted enters the secretory pathway in the host cells and undergoes appropriate processings such as formation of disulfide bonds and glycosylation.

However, few signal sequences that effectively function in the fission yeast have been reported (Tokunaga, M. et al., Yeast 9, 379–387, 1993; Bröker, M. et al., B.B.A. 908, 203–213, 1987), no secretory expression vectors have been practically developed. On the other hand, the present inventors studied P-factor, which is a protein secreted by *S. pombe* from the cells and involved in mating as a mating pheromone. As a result, they found the fact that after conversion from its precursor by various enzymes in *S. pombe*, P-factor is secreted into a culture medium. They also determined the amino acid sequence and the gene of the P-factor precursor (Imai, Y. and Yamamoto, M., Gene & Dev. 8, 328–338; Japanese Unexamined Patent Publication No. 327481/1994). The amino acid sequence of the P-factor precursor is SEQ ID NO: 1 in the Sequence Listing give afterwards.

DISCLOSURE OF INVENTION

The present inventors focused on the above-mentioned P-factor and tried to develop a secretory expression vector by utilizing its secretory property. Though, it had been unknown which regions of the precursor function effectively as secretion signals as a result of further studies the present inventors found the N-terminal about 60 amino acids of the P-factor precursor functions effectively as secretion signals. As a result of more detail studies, they found the existence of a presequence which is to be cut off by signal peptidase, and a prosequence, which is to be cut off by proteases in the endoplasmic reticulum or the Golgi apparatus during processing. Accordingly, the secretion signal of the P-factor precursor can be shorter than the N-terminal about 60 amino acids.

The present invention provides a gene encoding for a polypeptide functional as a secretion signal in *S. pombe*. The polypeptide may be a polypeptide identical, equivalent or analogous to the secretion signal of the P-factor precursor or a longer polypeptide containing the polypeptide (but shorter than the P-factor precursor itself). The polypeptide may have at least one extra amino acid residue that the secretion signal of the P-factor precursor does not inherently have, or have at least one different amino acid residues substituted for at least one amino acid residue in the secretion signal of the P-factor precursor. Further, the polypeptide may lack at least one amino acid residue in the secretion signal of the P-factor precursor. Hereinafter, a polypeptide functional as a secretion signal in S. *pombe* is referred to simply as the secretion signal.

The present invention relates to a gene encoding the secretion signal (hereinafter referred to as secretion signal gene), a multicloning vector having the secretion signal gene, an expression vector having the secretion signal gene and a foreign protein structural gene, a transformant from a eucaryotic host which carries a recombinant DNA having the secretion signal gene or the expression vector, and a method of producing a foreign protein by using the transformant. The present invention provides:

- a secretion signal gene having a base sequence encoding a polypeptide functional as a secretion signal in S. *pombe*;
- a secretion signal gene having a base sequence encoding a secretion signal of the P-factor precursor produced by S. *pombe* or a polypeptide containing the amino acid sequence of the secretion signal and functional as a secretion signal in S. *pombe*, in which one or more addition, deletion or substitution of at least amino acid residue have been made;
- a secretion signal gene having a base sequence encoding a polypeptide having an amino acid sequence from the 1st amino acid to the 16–160th amino acid of SEQ ID NO: 1, wherein addition, deletion or substitution of at least amino acid residue may have been made;
- a secretion signal gene having a base sequence encoding a polypeptide having an amino acid sequence from the 1st amino acid to the 22±6th, the 31±6th or the 57±6th amino acid of SEQ ID NO: 1, wherein addition, deletion or substitution of at least amino acid residue may have been made;
- a secretion signal gene having a base sequence encoding the above polypeptide, wherein the polypeptide has at least one additional amino acid residue at the carboxy terminus so as to have a carboxy-terminal amino acid sequence of [-Lys-Lys-Arg];
- a multicloning vector for construction of an expression vector for expression of a foreign protein in a eucaryotic host cell, which has the above-mentioned secretion signal gene upstream from a foreign protein structural gene introduction site so that the secretion signal gene can be directly ligated with a foreign protein structural gene to be introduced;
- an expression vector to be expressed in an eucaryotic host, which has a structural gene of a protein combination of a secretion signal and a foreign protein bonded together in this order from the amino terminus, wherein the gene of the secretion signal is the above-mentioned secretion signal gene;
- a transformant from a eucaryotic host cell, which carries a recombinant DNA containing a structural gene of a protein combination of the above secretion signal gene and a foreign protein bonded together in this order from the amino terminus, or the above expression vector; and
- a method of producing a foreign protein, which comprises culturing the transformant so that the foreign protein is produced and accumulated in the culture, and collecting it.

In a transformant having the secretion signal gene of the present invention, a foreign protein synthesized with a secretion signal bonded is cut in the cells so as to shed the secretion signal, and is secreted from the cells. Therefore, it is possible to obtain a desired protein by isolating it from the culture medium, and to produce a desired protein effectively and easily.

According to the present inventors' studies, the longest secretion signal in Examples is a polypeptide segment of up to the 57th amino acid. However, in the present invention the secretion signal may be a longer polypeptide segment containing this polypeptide (in Example 1, a polypeptide of up to the 59th amino acid was used). In this case, a foreign protein is secreted with amino acid residues in the polypeptide segment downstream from the cleaved site (hereinafter referred to as additional segment) bonded. The object of the present invention can be achieved, when the secreted protein is useful or at least not adverse (for example, when the additional segment can be removed afterward) even if the intended foreign protein is secreted with the additional segment bonded to it. Further, considering the sequence from the 55th amino acid to the 59th amino acid of the polypeptide segment, where the polypeptide segment is cleaved, the sequence of the first about 160 amino acid residues contains three more sequences similar to the sequence from the 55th to the 59th amino acid, and it is anticipated that the cleavage can occur also at these three sites.

However, in general, a long additional segment is likely to be adverse to the desired foreign protein. Accordingly, it is preferred that the secreted protein contains no additional segment or a short additional segment. In this sense, an expression vector preferably is so constructed as to induce expression of a foreign protein bonded to a sequence having an amino acid sequence of the first at most 160 amino acids of SEQ ID NO: 1 containing a secretion signal, more preferably to a sequence having the amino acid sequence (SEQ ID NO: 2), which corresponds to the first at most 59 amino acids of SEQ ID NO: 1. The results of Examples show that when the secretion signal has an amino acid sequence of up to the 59th amino acid, the secreted foreign protein has the 58th and 59th amino acid residues of the secretion signal at the amino terminus. Therefore, in this case, it is anticipated that a polypeptide from the 1st amino acid to the 57th amino acid of SEQ ID NO: 1 (or, of SEQ ID NO: 2) is more suitable as a secretion signal.

Cleavage occurs behind from the 55th amino acid to the 57th amino acid sequence of [-Lys-Lys-Arg-]. Therefore, it is anticipated that this sequence is a kind of cleavage signal. This suggest that cleavage also can occur behind the sequences of [-Lys-Lys-Arg-] from the 89th amino acid to the 91st amino acid, from the 123rd amino acid to the 125th amino acid and from the 157th amino acid to the 159th amino acid.

Further, a detailed study on the secretion signal aimed at use of a shorter sequence revealed that the amino acid sequence from the amino terminus to the 22nd amino acid constitutes the presequence, and the amino acid sequence from the 23rd (or the 25th) amino acid to the 31st amino acid constitutes the prosequence. Both the presequence and the prosequence can lead a desired protein bonded directly behind them to secretion. Therefore they are also useful as secretion signals, even though they are shorter than a sequence of the first about 60 amino acids from the amino terminus. On the other hand, according to a theoretical prediction, (von Heijne, G. "A new method for predicting signal sequence cleavage sites", Nucleic Acids Research, 14, 4683–4690 (1986)), the 16th [-Ala] and the 18th [-Pro] are possible rear ends of secretion signals shorter than the sequence of up to the 22nd amino acid. Therefore it is anticipated that a polypeptide having an amino acid sequence from the 1st amino acid to the 16th amino acid and a polypeptide having an amino acid sequence from the 1st amino acid to the 18th amino acid also can function as secretion signals.

A more detailed study revealed that the polyamino acid segment of from the amino terminus to about the 60th amino acid is cleaved in a higher probability especially at the carboxy terminus of the 57th Arg than the presequence of up to the 22nd (or the 24th) amino acid and the prosequence of up to the 31st amino acid. Therefore, in the case of a secretion signal of a short sequence, attachment of the sequence of [-Lys-Lys-Arg-] of from the 55th amino acid to the 57th amino acid directly behind the presequence or the prosequence leads to easier cleavage and is expected to efficient secretion. Actually, it is demonstrated that attachment of [-Lys-Arg] directly behind the 31st [-Lys-] improves efficiency of secretly production.

From the above, it is thought that the P-factor precursor is cleaved just behind the 22nd (or the 24th), the 31st and the 57th amino acids, and the polypeptides having the sequences of from the fist amino acid to these amino acids can function as secretion signals in S. pombe. Further, it is anticipated that longer or shorter sequences can also function as secretion signals in S. pombe. Therefore, the secretion signals of the present invention are primarily identical to these secretion signals of the P-factor precursor. The secretion signals of the present invention are polypeptides obtained by adding some amino acid residues to the C-termini of these polypeptides (such as the above-mentioned polypeptides of from the 1st amino acid to the 59th amino acid and Secretion Signal P2 Sequence which will be described later in Examples) and polypeptides obtained by deleting some amino acid residues at the C-termini of these polypeptides (such as Secretion Signal P1 Sequence which will be described later in Examples). Polypeptides obtained by substituting some amino acid residues of these polypeptides with other amino acid residues (such as amino acid residues analogous to the amino acid residues to be substituted in properties) also can function as secretion signals.

More preferred secretion signals are (a) a polypeptide having a sequence from the 1st amino acid to the 22nd (or the 25th) amino acid, (b) a polypeptide having a sequence of from the 1st amino acid to the 31st amino acid, (c) a polypeptide having a sequence of from the 1st amino acid to the 57th amino acid, (d) polypeptides which have the C-termini ±6 residues (preferably ±3 residues) of the C-termini of the polypeptides (a) to (c), and (e) a polypeptides which correspond to polypeptide (a), (b) or (d) which has at least one additional amino acid residue so as to have the sequence of [Lys-Lys-Arg] at the C-terminus. In the case of (e), the number of additional amino acid residues is preferably at most 5.

The secretion signal gene of the present invention is a gene encoding the above-mentioned secretion signal. This secretion signal gene means genes corresponding to upstream regions of the gene of the P-factor precursor disclosed in Japanese Unexamined Patent Publication No. 327481/1994 and its modified versions. The secretion signal gene is obtainable both from a S. pombe chromosome and by synthesis. The secretion signal gene is by no means restricted to the sequences disclosed in the above-mentioned publication, and may be genes having sequences encoding the amino acid sequences described above.

A desired foreign protein is expressed though an expression system containing its structural gene. As the expression system, a eucaryotic cell transformed with an expression vector containing a foreign protein structural gene is preferred. As the eucaryotic cell, S. pombe is particularly preferred. In the expression system, the above-mentioned secretion signal gene is linked to the front end of the foreign protein structural gene, and a protein combination of the secretion signal and the foreign protein bonded together is produced. After intracellular processing, the foreign protein is secreted out of the cell.

The multicloning vector of the present invention is a multicloning vector for construction of the expression vector which will be described below and enables expression of a foreign protein in a eucaryotic host cell. By introducing a foreign protein structural gene into the multicloning vector, the expression vector described below can be constructed. The expression vector described below means those constructed by using the secretion signal-foreign protein gene described below, and is not restricted to those constructed by using the multicloning vector of the present invention.

The multicloning vector of the present invention has the secretion signal gene described above upstream from a foreign protein structural gene introduction site so that the secretion signal gene can be ligated directly with a foreign protein structural gene to be introduced. When a foreign protein structural gene is introduced into it to constitute an expression vector, the secretion signal gene and the foreign protein structural gene are ligated and its expression of the ligation product produces a protein combination of the secretion signal and the foreign protein bonded together.

The expression vector of the present invention has a gene corresponding to the above-mentioned secretion signal and a foreign protein structural gene ligated together (hereinafter referred to as secretion signal-foreign protein gene) and enables expression of the gene in a eucaryotic host cell. This expression vector can be constructed by various methods by using the secretion signal-foreign protein structural gene. For example, it can be constructed by introducing a secretion signal-foreign protein gene at the multicloning site of a multicloning vector other than the multicloning vector of the present invention. It can be constructed without using a multicloning vector.

The expression vector of the present invention is preferably an expression vector having the structure disclosed in the above-mentioned Japanese Unexamined Patent Publication No. 15380/1993. It is preferred to construct the expression vector of the present invention by using the above-mentioned multicloning vector, which is disclosed in the specification of Japanese Patent Application No. 241581/1994, which relates to this expression vector or the method of constructing an expression vector using the multicloning vector. Nevertheless, the expression vector of the present invention may be an expression vector other than the expression vector disclosed in the above-mentioned publication, and may be of a chromosome integration type or of a type that can increase the copy number and can be present stably outside the nucleus. The expression vector of the present invention which has the structure disclosed in Japanese Unexamined Patent Publication No. 15380/1993 will be described below. However, the expression vector of the present invention is by no means restricted to it.

The expression vector of the present invention has a promoter region which controls the expression of the secretion signal-foreign protein gene introduced. The promoter governs the expression of the secretion signal-foreign protein gene introduced downstream. The promoter is capable of functioning in a eucaryotic cell and accelerates transcription of the introduced secretion signal-foreign protein gene. Specifically, a promoter which can function in *S. pombe* cells is preferred.

As such a promoter, for example, alcohol dehydrogenase gene promoter, human cytomegalovirus gene promoter and human chorionic gonadotropin α gene promoter may be mentioned. Particularly preferred are promoters which strongly accelerate transcription, such as promoters from animal viruses (R. Toyama et al., FEBS Lett, 268, 217–221 (1990)). As such a preferable promoter, promoters from animal viruses, particularly human cytomegalovirus gene promoter may be mentioned.

The expression vector of the present invention may have a drug resistance gene such as an antibiotic resistance gene and other various genes. Further, it is also possible to make the vector of the present invention a shuttle vector by incorporating a promoter or a drug resistance gene capable of functioning in a procaryotic cell such as *E. coli*.

An expression vector must have a replication origin in order to be expressed in cells. However, for the expression vector of the present invention, it is not always necessary to have a replication origin. A replication origin can be introduced after the expression vector has been constructed. It is also possible to autonomously introduce a replication origin into an expression vector having no replication origin in a cell after the expression vector is taken up by the cell. These methods of introducing a replication origin are already known. For example, a vector having a replication origin capable of functioning in a yeast (hereinafter referred as a yeast vector) can be integrated with the expression vector of the present invention (Japanese Unexamined Patent Publication No. 15380/1993). It is also possible to let the expression vector of the present invention and a yeast vector fuse together in cells autonomously by introducing them into the same cells. Since these method of introducing a replication origin are available, it is not critical whether the expression vector of the present invention has a replication origin or not. However, in any case for expression of the expression vector in cells, it is necessary that the vector ultimately has a replication origin.

It is usually essential to introduce a drug resistance gene such as an antibiotic resistance gene into an expression vector as a marker or for cloning. A gene which releases a leucine-requiring cell from the necessity for leucine (such as LEU2 gene) or a gene which releases a uracil-requiring cell from the necessity for uracil (such as URA3 gene) is often introduced. It is preferred also for the vector of the present invention to have an antibiotic resistance gene and a promoter which accelerates the transcription of the antibiotic resistance gene (hereinafter referred to as a second promoter). The second promoter is preferred to have a lower transcription accelerating activity than the promoter that accelerates the transcription of the above-mentioned secretion signal-foreign protein gene. As the second promoter, promoters from animal viruses are preferred. Particularly preferred is SV40 early promoter. Although the antibiotic resistance gene governed by the second promoter may be a conventional one, particularly in the present invention, neomycin resistance gene is preferred.

In the present invention, by the use of the expression vector having an antibiotic resistance gene, it is possible to increase the expression amount of the secretion signal-foreign protein gene. For this purpose, the transcription accelerating activity of the second promoter must be lower than that of the promoter that governs the secretion signal-foreign protein gene. For the purpose of explanation, the case of culturing *S. pombe* that carries an expression vector having SV40 early promoter and neomycin resistance gene governed by the promoter is given as an example. When the *S. pombe* transformant is cultured in a medium containing G418 (neomycin), the copy number of the expression vector in a cell increases with G418 concentration in the medium. Accordingly, by increasing the G418 concentration, it is possible to increase the copy number of the expression vector in a cell and thereby increase the expression amount of the secretion signal gene-foreign protein. If the activity of the second promoter is higher than the promoter governing the secretion signal-foreign protein gene, there is no need to increase the copy number of the expression vector since a small copy number of the vector is enough to induce production of a sufficient amount of neomycin resistance protein (enzyme), and therefore it is impossible to increase the expression amount of the desired secretion signal-foreign protein.

The foreign protein as the product of a foreign protein structural gene is not particularly restricted, but is preferably a physiologically active protein of a higher animal. For example, a glycoproteins which are basically obtainable by secretory production by an animal cell and difficult to produce by using *E. coli* and proteins having complicated steric structures with many disulfide bonds, such as human serum albumin and interleukin-6, are particularly preferred.

The general technique of constructing the multicloning vector or the expression vector of the present invention is already known and disclosed, for example, in a reference, J. Sambrook et al., "Molecular Cloning 2nd ed.", Cold Spring Harbor Laboratory Press (1989). The multicloning vector and the expression vector of the present invention can be constructed by the above-mentioned method by using this conventional technique. As a strain of *S. pombe* to be used in the present invention as a host for the expression vector, ATCC 38399 (leu1-32h$^-$) and ATCC 38436 (ura4-294h$^-$) may, for example, be mentioned. These strains are available from American Type Culture Collection.

*S. pombe* can be transformed by using an expression vector by known methods, and a *S. pombe* transformant can be obtained by, for example, the lithium acetate method (K. Okazaki et al., Nucleic Acids Res., 18, 6485–6489 (1990).). The transformant is cultured in a known medium, and nutrient media such as YPD medium, minimal media such as MM medium (M. D. Rose et al., "Methods In Yeast Genetics", Cold Spring Harbor Laboratory Press (1990).) and the like may be used. The transformant is cultured usually at from 16 to 42° C., preferably at from 25 to 37° C., for from 8 to 168 hours, preferably from 48 to 96 hours. Either of shaking culture and stationary culture can be employed, and, if necessary, the culture medium may be stirred or aerated.

As methods of isolating and purifying the protein produced in the culture, known methods, such as methods utilizing difference in solubility such as salting out and precipitation with a solvent, methods utilizing difference in molecular weight such as ultrafiltration and gel electrophoresis, methods utilizing difference in electric charge such as ion-exchange chromatography, methods utilizing specific affinity such as affinity chromatography, methods utilizing difference in hydrophobicity such as reverse phase high performance liquid chromatography, and methods utilizing difference in isoelectric point such as isoelectric focusing may be mentioned.

The isolated and purified protein can be identified by conventional methods such as western blotting or assay of its activity. The structure of the purified protein can be defined by amino acid analysis, amino-terminal analysis, primary structure analysis and the like.

BRIEF DESCRIPTION OF DRAWINGS

The accompanying drawings in association with the item best mode for carrying out the invention, are explained below.

BEST MODE OF CARRYING OUT THE INVENTION

Figure 1:
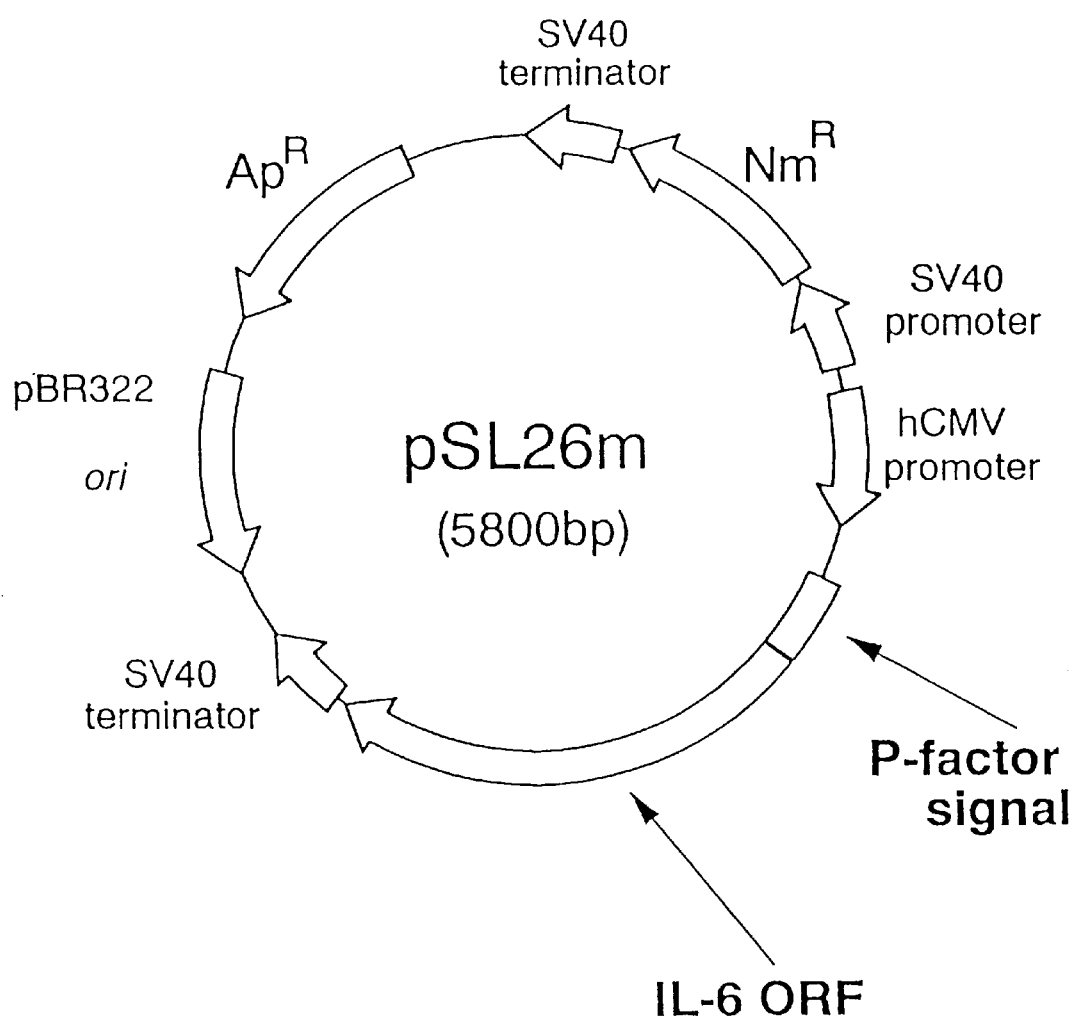
FIG. 1 illustrates the structure of the vector pSL26m, which was constructed in Example 1.

Now, the present invention will be described in further detail with reference to Examples. However, it should be understood that the technical scope of the present invention is by no means restricted to such specific examples.

Reference Examples 1 and 2 explain the methods of transforming and culturing a yeast employed in Examples.

REFERENCE EXAMPLE 1
Transformation of a yeast

A leucine-requiring strain, S. pombe leu1-32h$^-$ (ATCC38399) was used as the host. Host cells were grown in animal medium until the cell number became (0.5–1)×10$^7$ cells/ml. The cells were collected and suspended in 0.1M lithium acetate (pH 5) at a cell number of 1×10$^9$ cells/ml. Then, the cell suspension was incubated at 30° C. for 60 minutes. 1 μg of a PstI fragment of a yeast vector pAL7 (ars, stb, LEU) (Nucleic Acid Research 18, 6485–6489) and 2 μg of an expression vector obtained in Examples were added to 100 μl of the cell suspension, and 290 μl of 50% (W/V) PEG4000 (polyethylene glycol with a molecular weight of 4,000) was added, and they were mixed enough. Then, the mixture was incubated at 30° C. for 60 minutes and at 43° C. for 15 minutes and was allowed to stand at room temperature for 10 minutes. After removal of PEG4000 by centrifugation, the cells were suspended in an appropriate amount of a medium, and the suspension was spread on a minimum medium. The transformation ratio was at least 10$^5$ μg (pAL7).

An appropriate number of the transformants obtained above were harvested, and each transformant was suspended in 300 μl of water. A 3 μl portion of the suspension was spread on YEA medium (yeast extract 5 g, glucose 30 g, ager 20 g/l l containing G418 (25 μg/ml) and three days after, the colonies formed were picked up for use.

REFERENCE EXAMPLE 2
Culture of yeast

The transformed S. pombe (leu1-32h$^-$) strain was cultured in 5 μl of MM medium containing 1 wt % Casamino acid and 2 wt % glucose (Alfa et al. "Experiments with Fission Yeast" Cold Spring Harbor Laboratory Press 1993) the presence of G418 (25 μg/ml) at 32° C. overnight, and 5×10$^7$ cells withdrawn from the culture medium were added to 50 ml of MM medium containing G418 (200 μg/ml), 1 wt % Casamino acid and 2 wt % glucose and cultured at 32° C. for 48 hours. Then it was centrifuged to collect the culture medium.

EXAMPLE 1
Preparation of human interleukin-6 secretory vector

PCR was performed by using a plasmid pAG9-8-1 (Japanese Unexamined Patent Publication No. 224097/1995) obtained by introducing the whole cDNA of human interleukin-6 into a commercially available vector pUC19 (sold by Boehringer Co., Ltd.) as the template and oligo DNAs shown in SEQ ID NOs: 3 and 4 as primers to multiply the region containing the ORF (open reading frame) of mature interleukin-6. The fragment thus obtained was subjected to double digestion by restriction enzymes EcoRI (sold by Takara Shuzo Co.) and HindIII (sold by Takara Shuzo Co.) for terminal treatment. After agarose gel electrophoresis, the band corresponding to about 600 base pairs was excised, and a gene fragment insertion was isolated by the glass beads method by using DNA-PREP (sold by Asahi Glass Company Ltd.).

PCR was performed by using a plasmid pADMP2 (Japanese Unexamined Patent Publication No. 327481/1994) containing the whole map2 gene of S. pombe as the template, and oligo DNAs shown in SEQ ID NOs: 5 and 6 as primers to multiply the region containing P-factor secretion signal sequence. Double digestion by restriction enzymes BspHI (sold by New England Biolab Co.) and EcoRI for terminal treatment was followed acrylamide gel electrophoresis. The band corresponding to about 200 base pairs was excised, and a signal insertion fragment was eluted from the gel.

An expression vector pTL2M for S. pombe (Japanese Unexamined Patent Publication No. 163373/1995) constructed by using a vector pcD4B disclosed in Japanese Unexamined Patent Publication No. 15380/1993 was subjected to double digestion by restriction enzymes AflIII (sold by New England Biolab Co.) and HindIII, and then to agalose gel electrophoresis. The band corresponding to about 5,000 base pairs was excised, and a vector fragment was isolated by the glass beads method by using DNA-PREP.

These three fragments were ligated by means of a DNA ligation kit (Takara Shuzo Co.). E. coli DH5 strain (sold by Toyobo Co.) was transformed and screened for possession of the intended plasmid constructed properly. FIG. 1 illustrates the structure of the expression vector pSL26m thus obtained. pSL26m was prepared in a large amount by the alkali SDS method and identified by restriction map and partial base sequence analyzes as a plasmid having the intended sequence. The amino acid sequence of human interleukin-6 anticipated from the base sequence was SEQ ID NO: 7 and consisted of 185 residues. The amino acid sequence of the secretion signal sequence was SEQ ID NO: 2 and consisted of 59 residues.

EXAMPLE 2
Secretory production of human interleukin-6

Figure 2:
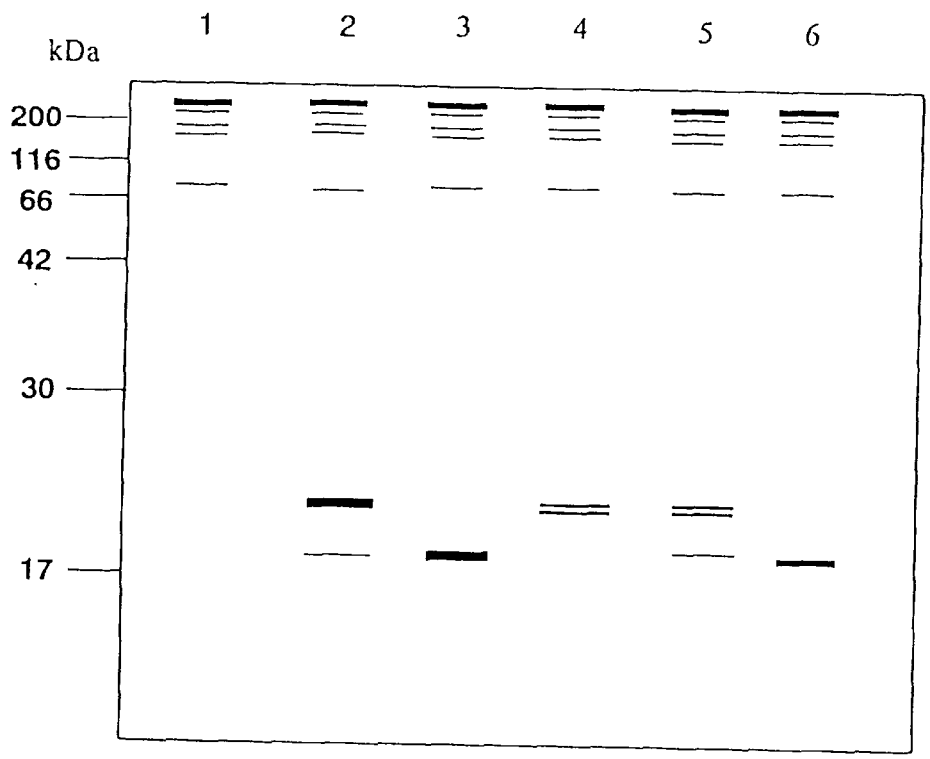
FIG. 2 and FIG. 3 show SDS-PAGE and western blotting patterns which demonstrate expression of human interleukin-6 and its variants obtained in Examples 2, 5, 8, 11 and 14.

Yeast was transformed with the secretory vector prepared in Example 1 in accordance with Reference Example 1 and then cultured in accordance with Reference Example 2. 50 ml of the culture medium was concentrated about 200 times by means of a membrane filter manufactured by Amicon Co., Ltd. The concentrated sample was analyzed by SDS-polyacrylamide gel electrophoresis followed by Coomassie Brilliant Blue staining. FIG. 2 shows the resulting SDS-PAGE pattern. In FIG. 2, lane 1 is the supernatant of *S. pombe*/pSL2M (control) culture, and lane 2 is the supernatant of *S. pombe*/pSL26m culture.

As shown in FIG. 2, several bands corresponding to molecular weights of at least 50,000 were observed, while in the low molecular weight region, a band at about 21K and another band at a little smaller molecular weight were mainly detected.

Figure 3:
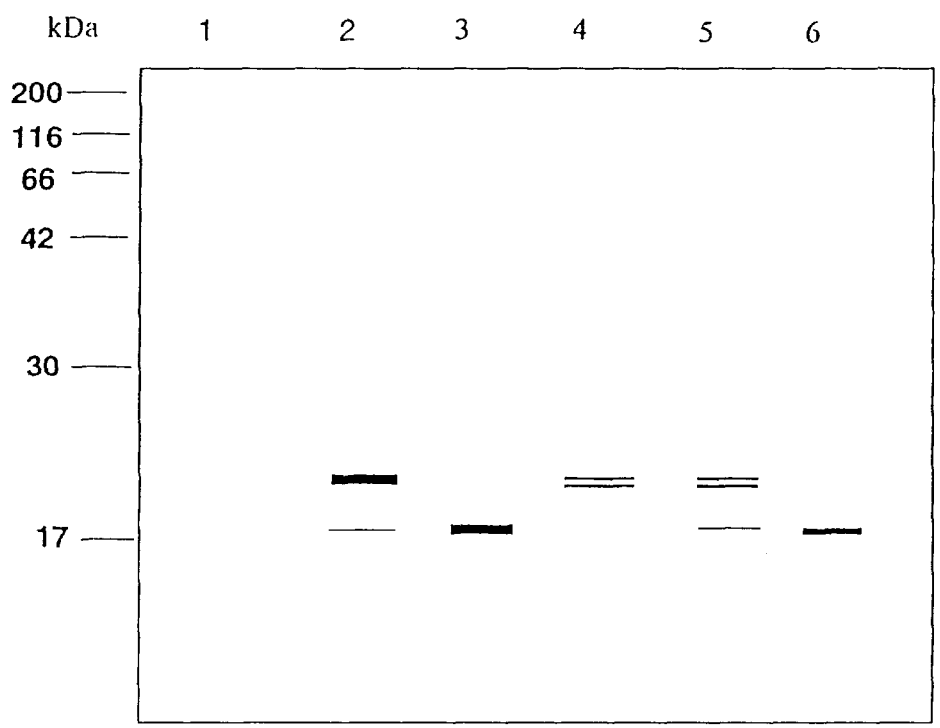

The results of western blotting analysis of the supernatants were shown in FIG. 3. In FIG. 3, lane 1 is the supernatant of *S. pombe*/pSL2M (control) culture, cutting and lane 2 is the supernatant of *S. pombe*/pSL26m culture. The bands at 21K and a little lower molecular weight were identified as attributed to human interleukin-6. Bands of little lower molecular weights seemed attributed to decomposition products.

EXAMPLE 3

Determination of the amino-terminal sequence of secreted protein

The protein isolated from the 21K band obtained by the SDS-PAGE electrophoresis in Example 2 was analyzed from the amino terminus by a protein sequencer ("Shimadzu PSQ-1") and found to have an amino terminal sequence of Glu-Phe-Met-Pro-Val-Pro-Pro- (SEQ ID NO: 30). This indicates that it is secreted into the medium after accurate processing between Lys and Glu of the secretion signal. Similar investigation of the minor band of a lower molecular weight revealed an extra cleavage between the 9th Lys and the 10th Asp.

EXAMPLE 4

Preparation of secretory vector for interleukin-6 variant by using secretion signal PCR was performed by using a plasmid pTL26a'C1 (Japanese Unexamined Patent Publication No. 224097/1995) containing the cDNA of a human interleukin-6 variant as the template and oligo DNAs represented by SEQ ID NOs: 8 and 9 to multiply a region containing the ORF of the interleukin-6 variant. The fragment thus obtained was subjected to double digestion by restriction enzymes EcoRI and HindIII for terminal treatment and then subjected to agalose gel electrophoresis. The band corresponding to about 600 base pairs was excised, and a gene insertion fragment was isolated by the glass beads method by using DNA-PREP.

A plasmid pSL26m (Example 1) containing cDNA of P-factor secretion signal sequence of *S. pombe* was subjected to double digestion by restriction enzymes EcoRI and HindIII for terminal treatment and then subjected to agalose gel electrophoresis. The band corresponding to 5,000 base pairs was excised, and a vector fragment was isolated by the glass beads method by using DNA-PREP.

Figure 4:
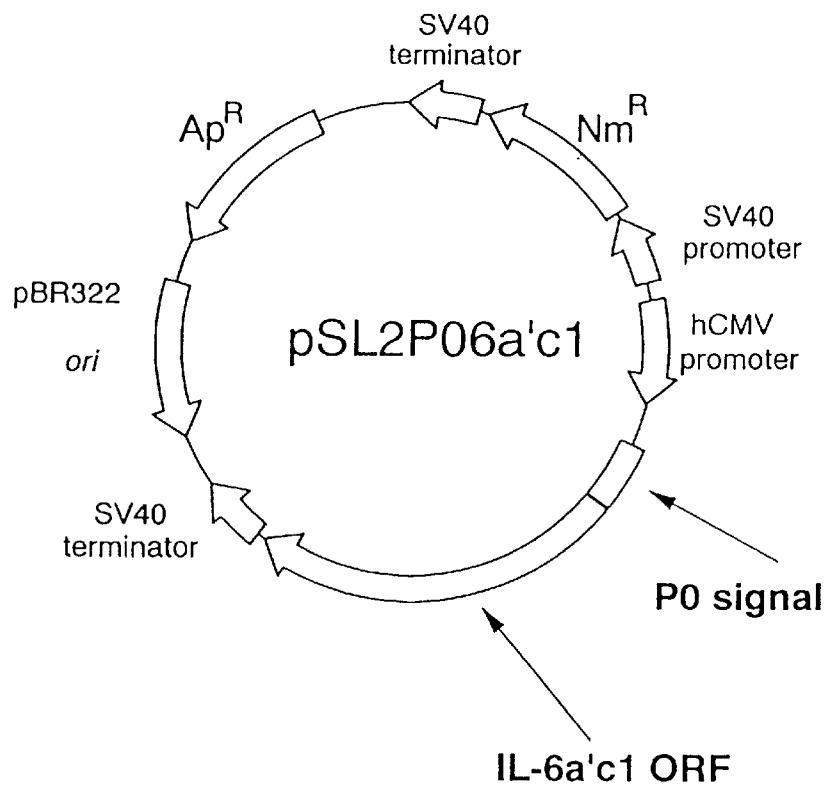
FIG. 4 illustrates the structure of the expression vector pSL2P06a'c1 constructed in Example 4.

The two fragments were ligated by means of a DNA ligation kit. After transformation of *E. coli* DH5 strain, the *E. coli* strain was screened for possession of the secretory vector pSL2P06a'C1 properly constructed as shown in FIG. 4 through restriction map analysis. pSL2P06a'C1 was prepared in a large amount by the alkali-SDS method, and the base sequences of the ORF of the interleukin-6 variant and the region corresponding to the P-factor secretion signal sequence were determined. As a result, the amino acid sequence of the interleukin-6 variant was expected from the base sequence to be represented by SED ID NO: 10 and consist of 162 residues, and the secretion signal sequence, which was designated as secretion signal "P0" sequence, was made of 59 residues and had an amino acid sequence represented by SEQ ID NO: 2.

EXAMPLE 5

Secretory production of human interleukin-6 variant by using secretion signal P0 sequence.

Yeast was transformed with the secretory vector prepared in Example 4 in accordance with Reference Example 1 and then cultured in accordance with Reference Example 2. 50 ml of the culture medium was concentrated about 200 times by means of a membrane filter manufactured by Amicon Co., Ltd. The concentrated sample was analyzed by SDS-polyacrylamide gel electrophoresis followed by Coomassie Brilliant Blue staining. FIG. 2 is the resulting SDS-PAGE pattern. In FIG. 2, lane 3 is the supernatant of *S. pombe*/pSL2P06a'C1 culture.

As shown in FIG. 3, while several bonds were detected in the region of molecular weight of at least 50,000, in the region of lower molecular weight, only one band was detected at about 18K.

The results of western blotting analysis of the supernatant of the culture are shown in FIG. 3. Lane 3 in FIG. 3 is the supernatant of the *S. pombe*/pSK2P06a'C1 culture. The band at 18K in lane 3 in FIG. 3 was identified as attributed to a human interleukin-6 variant (IL-6a'C1).

EXAMPLE 6

Determination of the amino-terminal sequence of secreted protein

The protein extracted by a conventional method from the band at 18K obtained by SDS-PAGE electrophoresis in Example 5 was analyzed from the amino terminus by a protein sequence ("Shimadzu PSQ-1") and found to have an amino terminal sequence of Glu-Phe-Pro-Val-Pro-Pro-Thr-Ser-Ser-Glu-(SEQ ID NO: 31". This indicates that IL-6a'C1, which is a variant which lacks the 9th and the 10th Lys-Asp from the N terminus of interleukin-6, is secreted into the medium after accurate processing between Lys and Glu of the secretion signal. Therefore, the extra cleavage in Example 3 is unnecessary to secretion, and unless a specific sequence is present in the molecule, only a type of protein with a constant terminus is secreted.

EXAMPLE 7

Preparation of secretory vector for interleukin-6 variant by using secretion signal P1 sequence PCR was performed by using a plasmid pSL2P06a'C1 (Example 4) containing the cDNA of a human interleukin-6 variant as the template and oligo DNAs represented by SEQ ID NOs: 11 and 12 to multiply a region containing the ORF of the interleukin-6 variant. The fragment thus obtained was subjected to double digestion by restriction enzymes HaeII (sold by Takara Shuzo co.) and HindIII for terminal treatment and then subjected to agarose gel electrophoresis. The band corresponding to about 500 base pairs was excised, and a gene insertion fragment was isolated by the glass beads method by using DNA-PREP.

PCR was performed by using a plasmid pSL2P06a'C1 (Example 4) containing the cDNA of the P-factor secretion signal sequence of *S. pombe* as the template, and oligo DNAs represented by SEQ ID NOs: 13 and 14 as primers to multiply a region containing the P-factor secretion signal sequence. The fragment thus obtained was subjected to double digestion by restriction enzymes SpeI (sold by Takara Shuzo Co.) and HaeII for terminal treatment and then subjected to agarose gel electrophoresis. The band corresponding to about 700 base pairs was excised, and a signal insertion fragment was isolated by the glass beads method by using DNA-PREP.

An expression vector pTL2M for *S. pombe* (Japanese Unexamined Patent Publication No. 163373/1995) was subjected to double digestion by restriction enzymes SpeI and HindIII for terminal treatment and subjected to agarose gel electrophoresis. The band corresponding to about 4,500 base pairs was excised, and a vector fragment was isolated by the glass beads method by using DNA-PREP.

Figure 5:
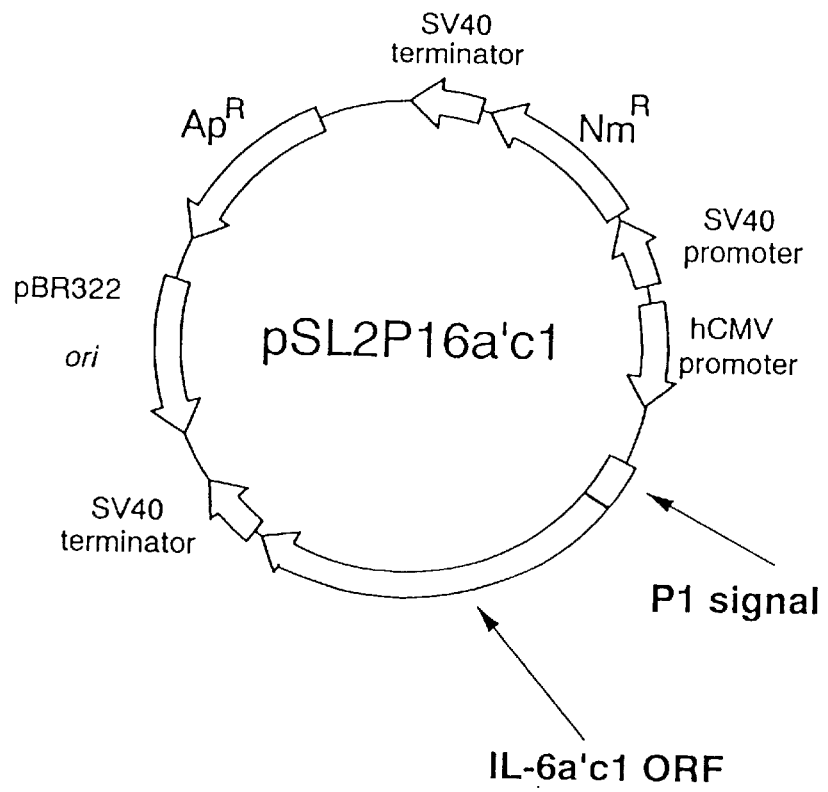
FIG. 5 illustrates the structure of the expression vector pSL2P16a'c1 constructed in Example 7.

These three fragments were ligated by means of a DNA ligation kit. After transformation of *E. coli* DH5 strain, *E. coli* clones were screened for possession of secretory vector pSL2P16a'C1 properly constructed as shown in FIG. 5 through restriction map analysis.

pSL2P16a'C1 was prepared in a large amount by the alkali-SDS method and the base sequences of the ORF of the interleukin-6 variant and the region corresponding to the P-factor secretion signal sequence were determined. From the base sequences, it is anticipated that the interleukin-6 variant has an amino acid sequence represented by SEQ ID NO: 15 and made of 163 residues, and the secretion signal sequence, which is designated as secretion signal "P1" sequence, has an amino acid sequence represented by SEQ ID NO: 16 and made of 30 residues.

EXAMPLE 8

Secretory production of human interleukin-6 variant by using secretion signal P1 sequence Yeast was transformed with the secretory vector prepared in Example 7 in accordance with Reference Example 1 and then cultured in accordance with Reference Example 2. 50 ml of the culture medium was concentrated about 200 times by means of a membrane filter manufactured by Amicon Co., Ltd. The concentrated sample was analyzed by SDS-polyacrylamide gel electrophoresis followed by Coomassie Brilliant Blue staining. FIG. 2 is the resulting SDS-PAGE pattern. In FIG. 2, lane 4 is the supernatant of *S. pombe*/pSL2P16a'C1 culture.

As shown in FIG. 2, while several bands were detected in the region of molecular weight of at least 50,000, in the region of lower molecular weight, two major bands were detected at about 19K.

The results of the western blotting analysis of the supernatant of the culture are shown in FIG. 3. In FIG. 3, lane 4 is the supernatant of the *S. pombe*/pSL2P16'C1 culture. The two bands at about 19K in lane 4 in FIG. 3 were identified as attributed to a human interleukin-6 variant IL-6a'C1.

EXAMPLE 9

Determination of the amino terminal sequence of the secreted protein

The amino terminal sequences of the proteins extracted by a conventional method from the two bands at about 19K obtained by SDS-PAGE electrophoresis in Example 5 were analyzed by means of a protein sequencer, and found to be Asp-PRo-Gly-Val-Val-Ser-Val-Ser-Ala-Pro-(SEQ ID NO: 32) for the upper band and Gly-Val-Val-Ser-Val-Ser-Ala-Pro-Val-Pro-(SEQ ID NO: 33) for the lower band. The results indicate that two cleavage sites are present, and that secretion signal P1 was cut between the 22nd Ala and the 23rd Asp from the N-terminus and between Pro and Gly, which are two residues closer to the C-terminus. It is highly probable that the secretion signal P1 sequence has two signal peptidase cleavage sites.

EXAMPLE 10

Preparation of interleukin-6 variant secretory vector by using secretion signal P2 sequence PCR was performed by using a plasmid pSL2P06a'C1 (Example 4) containing the cDNA of a human interleukin-6 variant as the template and oligo DNAs represented by SEQ ID NOs: 17 and 18 as primers to multiply the region containing the ORF of the interleukin-6 variant. The fragment thus obtained was subjected double digestion by restriction enzymes HaeII and HindIII for terminal treatment and then subjected to agarose gel electrophoresis. The band corresponding to about 500 base pairs was excised, and a gene insertion fragment was isolated by the glass beads method by using DNA-PREP.

PCR was performed by using a plasmid pSL2P06a'C1 (Example 4) containing the cDNA of P-factor secretion signal sequence of *S. pombe* as the template and oligo DNAs represented by SEQ ID NOs: 19 and 20 as primers to multiply the region containing the P-factor secretion signal sequence. The fragment thus obtained was subjected to double digestion by restriction enzymes SpeI and HaeII for terminal treatment and then to agalose gel electrophoresis. The band corresponding to about 700 base pairs was excised, and a signal insertion fragment was isolated by the glass beads method by using DNA-PREP.

An expression vector pTL2M for *S. pombe* (Japanese Unexamined Patent Publication No. 163373/1995) was subjected to double digestion by restriction enzymes SpeI and HindIII for terminal treatment and then to agalose gel electrophoresis. The band corresponding to about 4,500 base pairs was excised, and a vector fragment was isolated by the glass beads method by using DNA-PREP.

Figure 6:
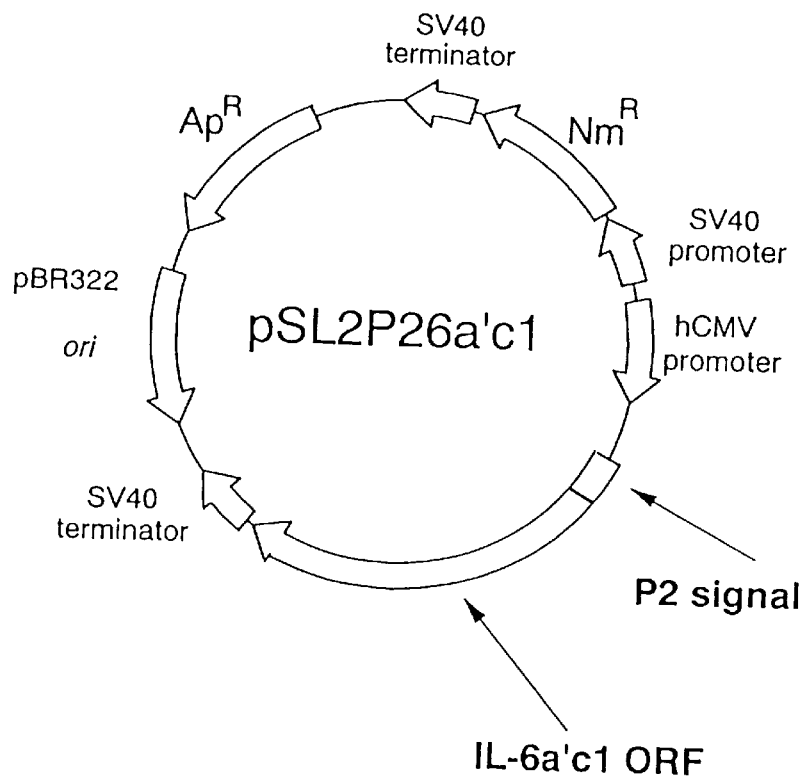
FIG. 6 illustrates the structure of the expression vector pSL2P26a'c1 constructed in Example 10.
Figure 7:
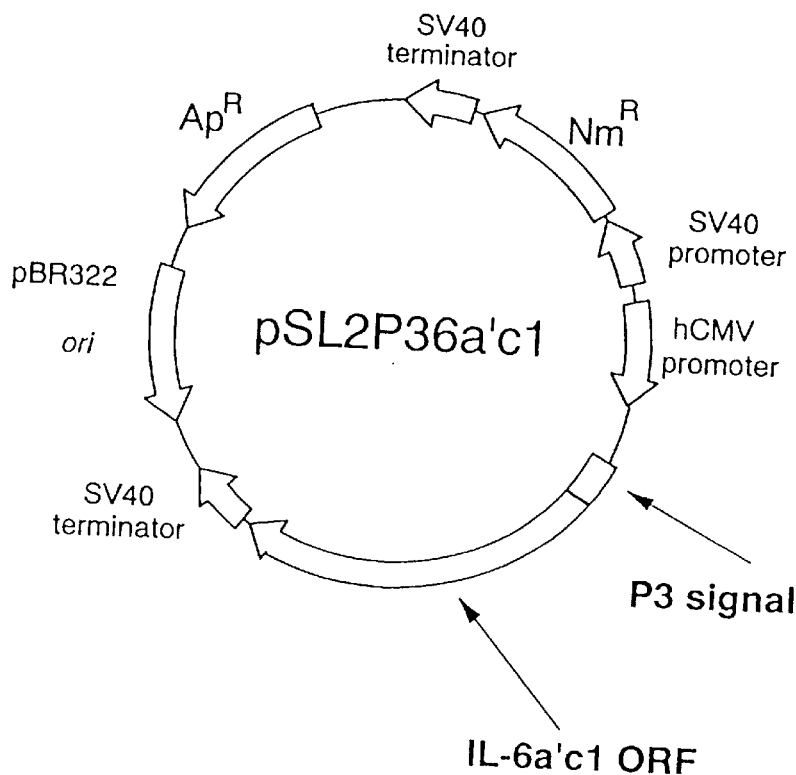
FIG. 7 illustrates the structure of the expression vector pSL2P36'c1 constructed in Example 13.

These three fragments were ligated by means of a DNA ligation kit. After transformation of *E. coli* DH5 strain, *E. coli* clones were screened for possession of secretory vector pSL2P26a'C1 properly constructed as shown in FIG. 6 by restriction map analysis.

pSL2P26a'C1 was prepared in a large amount by the alkali-SDS method, and the base sequences of the ORF of the interleukin-6 variant and the region corresponding to the P-factor secretion signal sequence were determined. From the base sequences, it is anticipated that the interleukin-6 variant has an amino acid sequence represented by SEQ ID NO: 15 and the secretion signal sequence, which is designated as secretion signal "P2" sequence, has an amino acid sequence represented by SEQ ID NO: 21 made of 31 residues.

EXAMPLE 11

Secretory production of human interleukin-6 variant by using secretion signal P2 sequence Yeast was transformed with the secretory vector prepared in Example 10 in accordance with Reference Example 1 and then cultured in accordance with Reference Example 2. 50 ml of the culture medium was concentrated about 200 times by means of a membrane filter manufactured by Amicon Co., Ltd. The concentrated sample was analyzed by SDS-polyacrylamide gel electrophoresis followed by h Coomassie Brilliant Blue staining. FIG. 2 shows the resulting SDS-PAGE pattern. In FIG. 2, lane 5 is the supernatant of *S. pombe*/pSL2P26a'C1 culture.

As shown in FIG. 2, while several bands were detected in the region of molecular weight of at least 50,000, in the region of lower molecular weight, two major bands and one main band were detected at about 19K and at about 18.5K, respectively.

The results of the western blotting analysis of the supernatant of the culture are shown in FIG. 3. In FIG. 3, lane 5 is the supernatant of the *S. pombe*/pSL2P26a'C1 culture. The two bands at about 19K and the band that about 18.5K in lane 5 in FIG. 3 were identified as attributed to human interleukin-6 variant IL-6a'C1.

EXAMPLE 12
Determination of the amino terminal sequence of the secreted protein The amino terminal sequences of the proteins extracted by a conventional method from the two bands at about 19K obtained by SDS-PAGE electrophoresis in Example 11 were analyzed by means of a protein sequencer, and found to be Asp-PRo-Gly-Val-Val-Ser-Val-Ser-Ala-Pro-(SEQ ID NO: 32) for the upper band and Gly-Val-Val-Ser-Val-Ser-Ala-Pro-Val-Pro-(SEQ ID NO: 33) for the lower band. The results indicate that two cleavage sites are present, and that secretion signal P1 was cut between the 22nd Ala and the 23rd Asp from the N-terminus and between Pro and Gly, which are two residues closer to the C-terminus. It is highly probable that the secretion signal has two signal peptidase cleavage sites. Further, the amino terminal sequence of the peptide extracted from the band at about 18.5K was analyzed from the N-terminus and found to be Ser-Ala-Pro-Val-Pro-Pro-Thr-Ser-Ser-Glu-(SEQ ID NO: 34). This indicates that the secretion signal P2 is cut between the 31st Lys and the 32nd Ser from the N-terminus during processing before secretion.

EXAMPLE 13
Preparation of interleukin-6 variant secretory vector by using secretion signal P3 sequence PCR was performed by using a plasmid pSL2P06a'C1 (Example 4) containing the cDNA of a human interleukin-6 variant as the template and oligo DNAs represented by SEQ ID NOs: 22 and 23 as primers to multiply a region containing the ORF of the interleukin-6 variant. The fragment thus obtained was subjected double digestion by restriction enzymes AflII (sold by Nippon Gene Co.) and HindIII for terminal treatment and then subjected to agarose gel electrophoresis. The band corresponding to about 500 base pairs was excised, and a gene insertion fragment was isolated by the glass beads method by using DNA-PREP.

PCR was performed by using a plasmid pSL2P06a'C1 (Example 4) containing the P-factor secretion signal sequence of S. pombe as the template and oligo DNAs represented by SEQ ID NOs: 24 and 25 as primers to multiply a region containing the P-factor secretion signal sequence. The fragment thus obtained was subjected to double digestion by restriction enzymes SpeI and AflII for terminal treatment and then to agalose gel electrophoresis. The band corresponding to about 700 base pairs was excised, and a signal insertion fragment was isolated by the glass beads method by using DNA-PREP.

An expression vector pTL2M for S. pombe (Japanese Unexamined Patent Publication No. 163373/1995) was subjected to double digestion by restriction enzymes SpeI and HindIII for terminal treatment and then to agalose gel electrophoresis. The band corresponding to about 4,500 base pairs was excised, and a vector fragment was isolated by the glass beads method by using DNA-PREP.

These three fragments were ligated by means of a DNA ligation kit. After transformation of E. coli DH5 strain, E. coli clones were screened for possession of secretory vector pSL2P36a'C1 properly constructed as shown in FIG. 6 through restriction map analysis.

pSL2P36a'C1 was prepared in a large amount by the alkali-SDS method, and the base sequences of the ORF of the interleukin-6 variant and the region corresponding to the P-factor secretion signal sequence were determined. From the base sequences, it is anticipated that the interleukin-6 variant has an amino acid sequence represented by SEQ ID NO: 15 and the secretion signal sequence, which is designated as secretion signal "P3" sequence, has an amino acid sequence represented by SEQ ID NO: 26 made of 34 residues.

EXAMPLE 14
Secretory production of human interleukin-6 variant by using secretion signal P3 sequence.

Yeast was transformed with the secretory vector prepared in Example 13 in accordance with Reference Example 1 and then cultured in accordance with Reference Example 2. 50 ml of the culture medium was concentrated about 200 times by means of a membrane filter manufactured by Amicon Co., Ltd. The concentrated sample was analyzed by SDS-polyacrylamide gel electrophoresis followed by the Coomassie Brilliant Blue staining. FIG. 2 is the resulting SDS-PAGE pattern. In FIG. 2, lane 6 is the supernatant of S. pombe/pSL2P36a'C1 culture.

As shown in FIG. 2, while several bands were detected in the region of molecular weight of at least 50,000, in the region of lower molecular weight, one band was detected at about 18K.

The results of the western blotting analysis of the supernatant of the culture are shown in FIG. 3. The band at about 18K in lane 6 in FIG. 3 was identified as attributed to IL-6a'C1.

EXAMPLE 15
Determination of the amino-terminal sequence of the secreted protein The N-terminal sequence of the protein isolated by a conventional method from the band at 20K obtained by the SDS-PAGE electrophoresis in Example 14 was analyzed by a protein sequencer and found to be Ala-Pro-Val-Pro-Pro-Thr-Ser-Ser-Glu-(SEQ ID NO: 35). This indicates that the protein is secreted into the medium after accurate processing between Lys at the terminus of P3 signal and Ala at the N-terminus of LI-6a'C1.

EXAMPLE 16
Preparation of general-purpose secretory vector

PCR was performed by using an expression vector pTL2M for S. pombe (Japanese Unexamined Patent Publication No. 163373/1995) as the template and oligo DNAs represented by the SEQ ID NOs: 27 and 28 as primers to multiply the region containing a MCS (multicloning site) sequence. The fragment thus obtained was subjected to double digestion by restriction enzymes AflIII and BglII (sold by Takara Shuzo Co.) for terminal treatment and then to agarose gel electrophoresis. The band corresponding to about 300 base pairs was excised, and a MCS insertion fragment was isolated by the glass beads method by using DNA-PREP.

A human interleukin-6 variant secretory vector pSL2P36a'C1 (Example 13) was subjected to double digestion by restriction enzymes AflII and BamHI (sold by Takara Shuzo Co.) for terminal treatment and then to agalose gel electrophoresis. The band corresponding to about 4,500 base pairs was excised, and a vector fragment was isolated by the glass beads method by These DNA-PREP.

Figure 8:
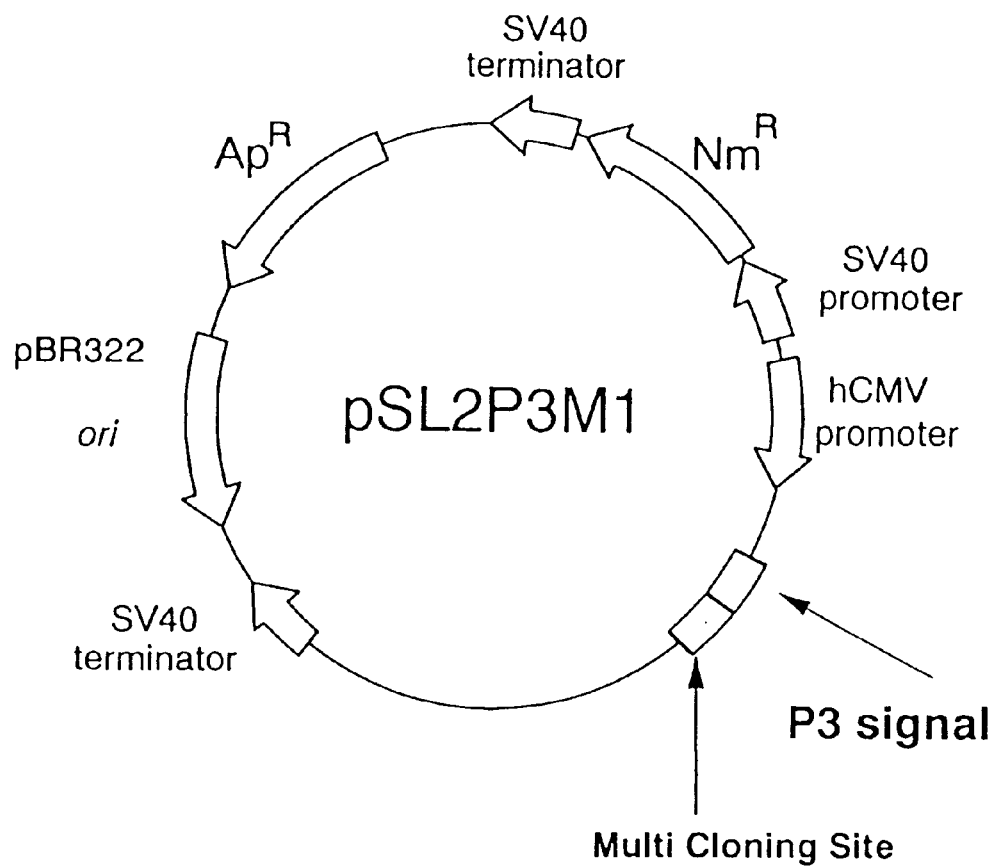
FIG. 8 illustrates the structure of the expression vector pSL2P3M1 constructed in Example 16.

These two fragments were ligated by means of a DNA ligation kit. After transformation of E. coli DH5 strain, E. coli clones were screened for possession of a secretory vector pSL2P3M1 constructed properly as shown in FIG. 8.

pSL2P3M1 was prepared in a large amount by the alkali-SDS method, and the base sequences of the MCS sequence and the region corresponding to the P-factor secretion signal sequence were determined. As a result, the MCS sequence has a base sequence of 75 bp represented by SEQ ID NO: 29, and it is anticipated from the base sequence that the amino acid sequence of the secretion signal sequence is represented by the SEQ ID NO: 26.

We claim:

1. A isolated polynucleotide sequence encoding a polypeptide functional as a secretion signal in *Schizosaccharomyces pombe*, wherein the polypeptide has an amino acid sequence from the $1^{st}$ amino acid residue to the $31\pm6^{th}$ amino acid residue of SEQ ID NO: 1, and the polypeptide has a carboxy-terminal amino acid sequence of Lys-Lys-Arg.

2. The isolated polynucleotide according to claim 1, wherein the polypeptide has the amino acid sequence of SEQ ID NO: 26.

3. A multicloning vector for an expression vector for expression of a foreign protein in a eucaryotic host cell, which has the polynucleotide according to claim 1 upstream from a foreign protein structural gene introduction site so that the polynucleotide of claim 1 can be directly ligated with a foreign protein structural gene to be into the vector.

4. An expression vector to be expressed in a eucaryotic host cell, such that the polynucleotide of claim 1 and a structural gene are bonded together at the end corresponding to the amino terminus of the foreign protein.

5. The expression vector according to claim 4, which has an animal virus-derived promoter region expression of the foreign protein structural gene.

6. The expression vector according to claim 4, a polynucleotide encoding a neomycine resistance region and a second animal virus-derived promoter expression of the neomycine resistance region.

7. The expression vector according to claim 4, wherein the eucaryotic host cell is *Schizosaccharomyces pombe*.

8. A transformed eucaryotic host cell, which carries the expression vector according to claim 4.

9. The transformant according to claim 8, wherein the eucaryotic host cell is *Schizosaccharomyces pombe*.

10. A method of producing a foreign protein, which comprises culturing the transformant of claim 8 so that the foreign protein is produced and accumulated in the culture, and collecting it.

* * * * *

SEQUENCE LISTING (1) GENERAL INFORMATION:

(iii) NUMBER OF SEQUENCES: 35

(2) INFORMATION FOR SEQ ID NO:1:

(i) SEQUENCE CHARACTERISTICS:
        (A) LENGTH: 201 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:1:

Met Lys Ile Thr Ala Val Ile Ala Leu Leu Phe Ser Leu Ala Ala Ala
1               5                   10                  15

Ser Pro Ile Pro Val Ala Asp Pro Gly Val Val Ser Val Ser Lys Ser
                20                  25                  30

Tyr Ala Asp Phe Leu Arg Val Tyr Gln Ser Trp Asn Thr Phe Ala Asn
            35                  40                  45

Pro Asp Arg Pro Asn Leu Lys Lys Arg Glu Phe Glu Ala Ala Pro Ala
50                  55                  60

Lys Thr Tyr Ala Asp Phe Leu Arg Ala Tyr Gln Ser Trp Asn Thr Phe
65                  70                  75                  80

Val Asn Pro Asp Arg Pro Asn Leu Lys Lys Arg Glu Phe Glu Ala Ala
                85                  90                  95

Pro Glu Lys Ser Tyr Ala Asp Phe Leu Arg Ala Tyr His Ser Trp Asn
            100                 105                 110

Thr Phe Val Asn Pro Asp Arg Pro Asn Leu Lys Lys Arg Glu Phe Glu
        115                 120                 125

Ala Ala Pro Ala Lys Thr Tyr Ala Asp Phe Leu Arg Ala Tyr Gln Ser
    130                 135                 140

Trp Asn Thr Phe Val Asn Pro Asp Arg Pro Asn Leu Lys Lys Arg Thr
145                 150                 155                 160

Glu Glu Asp Glu Glu Asn Glu Glu Asp Glu Glu Tyr Tyr Arg Phe
                165                 170                 175

Leu Gln Phe Tyr Ile Met Thr Val Pro Glu Asn Ser Thr Ile Thr Asp
            180                 185                 190

Val Asn Ile Thr Ala Lys Phe Glu Ser
            195                 200

(2) INFORMATION FOR SEQ ID NO:2:

(i) SEQUENCE CHARACTERISTICS:
        (A) LENGTH: 59 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Met Lys Ile Thr Ala Val Ile Ala Leu Leu Phe Ser Leu Ala Ala Ala
1               5                   10                  15

Ser Pro Ile Pro Val Ala Asp Pro Gly Val Val Ser Val Ser Lys Ser
                20                  25                  30

Tyr Ala Asp Phe Leu Arg Val Tyr Gln Ser Trp Asn Thr Phe Ala Asn
            35                  40                  45

Pro Asp Arg Pro Asn Leu Lys Lys Arg Glu Phe
    50                  55

(2) INFORMATION FOR SEQ ID NO:3:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:3:

GAATTCATGC CAGTACCCCC AGGAGAAGAT                                30

(2) INFORMATION FOR SEQ ID NO:4:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:4:

AAGCTTATTA CATTTGCCGA AGAGCCCTCA G                              31

(2) INFORMATION FOR SEQ ID NO:5:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:5:

CGGTCATGAA GATCACCGCT GTCAT                                     25

(2) INFORMATION FOR SEQ ID NO:6:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:6:

GGGAAGCTTA GCTCTCAAAT TTGGCAG                                   27

(2) INFORMATION FOR SEQ ID NO:7:

(i) SEQUENCE CHARACTERISTICS:
        (A) LENGTH: 185 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Met Pro Val Pro Pro Gly Glu Asp Ser Lys Asp Val Ala Ala Pro His
 1               5                  10                  15

Arg Gln Pro Leu Thr Ser Ser Glu Arg Ile Asp Lys Gln Ile Arg Tyr
             20                  25                  30

Ile Leu Asp Gly Ile Ser Ala Leu Arg Lys Glu Thr Cys Asn Lys Ser
             35                  40                  45

Asn Met Cys Glu Ser Ser Lys Glu Ala Leu Ala Glu Asn Asn Leu Asn
     50                  55                  60

Leu Pro Lys Met Ala Glu Lys Asp Gly Cys Phe Gln Ser Gly Phe Asn
65                   70                  75                  80

Glu Glu Thr Cys Leu Val Lys Ile Ile Thr Gly Leu Leu Glu Phe Glu
             85                  90                  95

Val Tyr Leu Glu Tyr Leu Gln Asn Arg Phe Glu Ser Ser Glu Glu Gln
            100                 105                 110

Ala Arg Ala Val Gln Met Ser Thr Lys Val Leu Ile Gln Phe Leu Gln
            115                 120                 125

Lys Lys Ala Lys Asn Leu Asp Ala Ile Thr Thr Pro Asp Pro Thr Thr
130                 135                 140

Asn Ala Ser Leu Leu Thr Lys Leu Gln Ala Gln Asn Gln Trp Leu Gln
145                 150                 155                 160

Asp Met Thr Thr His Leu Ile Leu Arg Ser Phe Lys Glu Phe Leu Gln
                165                 170                 175

Ser Ser Leu Arg Ala Leu Arg Gln Met
            180                 185

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:8:

AAAGAATTCC CAGTACCCCC AACCTCTTCA                                    30

(2) INFORMATION FOR SEQ ID NO:9:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:9:

AAGCTTATTA CATTTGCCGA GAGCCCTCA G                                   31

(2) INFORMATION FOR SEQ ID NO:10:

(i) SEQUENCE CHARACTERISTICS:
        (A) LENGTH: 162 amino acids
        (B) TYPE: amino acid
        (C) STRANDEDNESS: single
        (D) TOPOLOGY: linear (ii) MOLECULE TYPE: protein
```

(xi) SEQUENCE DESCRIPTION: SEQ ID NO:10:

Pro Val Pro Pro Thr Ser Ser Glu Arg Ile Asp Lys Gln Ile Arg Tyr
1               5                   10                  15

Ile Leu Asp Gly Ile Ser Ala Leu Arg Lys Glu Thr Glu Ser Ser Lys
            20                  25                  30

Glu Ala Leu Ala Glu Asn Asn Leu Asn Leu Pro Lys Met Ala Glu Lys
                35                  40                  45

Asp Gly Cys Phe Gln Ser Gly Phe Asn Glu Glu Thr Cys Leu Val Lys
            50                  55                  60

Ile Ile Thr Gly Leu Leu Glu Phe Glu Val Tyr Leu Glu Tyr Leu Gln
65                  70                  75                  80

Asn Arg Phe Glu Ser Ser Glu Glu Gln Ala Arg Ala Val Gln Met Ser
                85                  90                  95

Thr Lys Val Leu Ile Gln Phe Leu Gln Lys Lys Ala Lys Asn Leu Asp
            100                 105                 110

Ala Ile Thr Thr Pro Asp Pro Thr Thr Asn Ala Ser Leu Leu Thr Lys
                115                 120                 125

Leu Gln Ala Gln Asn Gln Trp Leu Gln Asp Met Thr Thr His Leu Ile
            130                 135                 140

Leu Arg Ser Phe Lys Glu Phe Leu Gln Ser Ser Leu Arg Ala Leu Arg
145                 150                 155                 160

Gln Met (2) INFORMATION FOR SEQ ID NO:11:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:11:

CTTGGCGCCC CAGTACCCCC AACCTCTTC                                      29

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:12:

AAAATGATTT AAAGGCTATA                                                20

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:13:

```
TTGACTAGTT ATTAATAGTA                                           20
```

(2) INFORMATION FOR SEQ ID NO:14:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:14:

```
CCAAGCGCTA ACTGAAACCA CACCAG                                    26
```

(2) INFORMATION FOR SEQ ID NO:15:

(i) SEQUENCE CHARACTERISTICS:
        (A) LENGTH: 163 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

```
Ala Pro Val Pro Pro Thr Ser Ser Glu Arg Ile Asp Lys Gln Ile Arg
1               5                   10                  15

Tyr Ile Leu Asp Gly Ile Ser Ala Leu Arg Lys Glu Thr Glu Ser Ser
                20                  25                  30

Lys Glu Ala Leu Ala Glu Asn Asn Leu Asn Leu Pro Lys Met Ala Glu
            35                  40                  45

Lys Asp Gly Cys Phe Gln Ser Gly Phe Asn Glu Glu Thr Cys Leu Val
        50                  55                  60

Lys Ile Ile Thr Gly Leu Leu Glu Phe Glu Val Tyr Leu Glu Tyr Leu
65                  70                  75                  80

Gln Asn Arg Phe Glu Ser Ser Glu Glu Gln Ala Arg Ala Val Gln Met
                85                  90                  95

Ser Thr Lys Val Leu Ile Gln Phe Leu Gln Lys Lys Ala Lys Asn Leu
            100                 105                 110

Asp Ala Ile Thr Thr Pro Asp Pro Thr Thr Asn Ala Ser Leu Leu Thr
        115                 120                 125

Lys Leu Gln Ala Gln Asn Gln Trp Leu Gln Asp Met Thr Thr His Leu
    130                 135                 140

Ile Leu Arg Ser Phe Lys Glu Phe Leu Gln Ser Ser Leu Arg Ala Leu
145                 150                 155                 160

Arg Gln Met
```

(2) INFORMATION FOR SEQ ID NO:16:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

```
Met Lys Ile Thr Ala Val Ile Ala Leu Leu Phe Ser Leu Ala Ala Ala
1               5                   10                  15

Ser Pro Ile Pro Val Ala Asp Pro Gly Val Val Ser Val Ser
```

(2) INFORMATION FOR SEQ ID NO:17:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:17:

CTTGGCGCCC CAGTACCCCC AACCTCTTC　　　　　　　　　　　　　　　　29

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:18:

AAAATGATTT AAAGGCTATA　　　　　　　　　　　　　　　　　　　　20

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:19:

TTGACTAGTT ATTAATAGTA　　　　　　　　　　　　　　　　　　　　20

(2) INFORMATION FOR SEQ ID NO:20:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:20:

CCAAGCGCTC TTGCTAACTG AAACCACAC　　　　　　　　　　　　　　　　29

(2) INFORMATION FOR SEQ ID NO:21:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

Met Lys Ile Thr Ala Val Ile Ala Leu Leu Phe Ser Leu Ala Ala Ala

```
 1               5                  10                 15
Ser Pro Ile Pro Val Ala Asp Pro Gly Val Val Ser Val Ser Lys Ser
            20                 25                 30
```

(2) INFORMATION FOR SEQ ID NO:22:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:22:

CCTCTTAAGA AGCGTCCAGT ACCCCCAACC TCTTC                35

(2) INFORMATION FOR SEQ ID NO:23:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:23:

AAAATGATTT AAAGGCTATA                20

(2) INFORMATION FOR SEQ ID NO:24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:24:

TTGACTAGTT ATTAATAGTA                20

(2) INFORMATION FOR SEQ ID NO:25:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:25:

CTTCTTAAGG CTAACTGAAA CCACACCAG                29

(2) INFORMATION FOR SEQ ID NO:26:

(i) SEQUENCE CHARACTERISTICS:
        (A) LENGTH: 34 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:26:

Met Lys Ile Thr Ala Val Ile Ala Leu Leu Phe Ser Leu Ala Ala Ala
1               5                   10                  15

Ser Pro Ile Pro Val Ala Asp Pro Gly Val Val Ser Val Ser Leu Lys
            20                  25                  30

Lys Arg (2) INFORMATION FOR SEQ ID NO:27:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:27:

TTTCTTAAGA AGCGTACATG TGAATTCGAG CTCGG                     35

(2) INFORMATION FOR SEQ ID NO:28:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:28:

AAAAGATCTG ATATCGTCTT GTGACGTCAT TTTATT                   36

(2) INFORMATION FOR SEQ ID NO:29:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:29:

CTTAAGAAGC GTACATGTGA ATTCGAGCTC GGTACCCGGG GATCCTCTAG AGTCGACCTG     60

CAGGCATGCA AGCTT                                                             75

(2) INFORMATION FOR SEQ ID NO:30:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:30:

Glu Phe Met Pro Val Pro Pro
1               5

(2) INFORMATION FOR SEQ ID NO:31:

(i) SEQUENCE CHARACTERISTICS:

(A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:31:

Glu Phe Pro Val Pro Pro Thr Ser Ser Glu
1               5                   10

(2) INFORMATION FOR SEQ ID NO:32:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:32:

Asp Pro Gly Val Val Ser Val Ser Ala Pro
1               5                   10

(2) INFORMATION FOR SEQ ID NO:33:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:33:

Gly Val Val Ser Val Ser Ala Pro Val Pro
1               5                   10

(2) INFORMATION FOR SEQ ID NO:34:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:34:

Ser Ala Pro Val Pro Pro Thr Ser Ser Glu
1               5                   10

(2) INFORMATION FOR SEQ ID NO:35:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:35:

Ala Pro Val Pro Pro Thr Ser Ser Glu
1               5